(12) United States Patent
Hori et al.

(10) Patent No.: US 7,557,059 B2
(45) Date of Patent: Jul. 7, 2009

(54) MULTICOMPONENT OXIDATION CATALYST AND PROCESS FOR PRODUCING EPOXY COMPOUND THEREWITH

(75) Inventors: Yoji Hori, Kanagawa (JP); Junji Nakamura, Kanagawa (JP); Tomoya Sawaki, Kanagawa (JP); Shigeru Tanaka, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 401 days.

(21) Appl. No.: 10/581,537

(22) PCT Filed: Nov. 24, 2004

(86) PCT No.: PCT/JP2004/017380
§ 371 (c)(1),
(2), (4) Date: Jun. 1, 2006

(87) PCT Pub. No.: WO2005/058494
PCT Pub. Date: Jun. 30, 2005

(65) Prior Publication Data
US 2007/0117993 A1      May 24, 2007

(30) Foreign Application Priority Data
Dec. 15, 2003   (JP) .............................. 2003-417188

(51) Int. Cl.
*B01J 31/00*      (2006.01)
*C07D 301/12*     (2006.01)
(52) U.S. Cl. ...................................... 502/160; 549/531
(58) Field of Classification Search .................. 549/531; 502/160
See application file for complete search history.

(56) References Cited

U.S. PATENT DOCUMENTS 4,562,276 A   12/1985   Venturello et al.
5,268,493 A   12/1993   Kayama et al.
5,780,655 A    7/1998   Shum
2002/0045791 A1  4/2002  Ninomiya et al.

FOREIGN PATENT DOCUMENTS

| | | |
|---|---|---|
| JP | 03-236343 | 10/1991 |
| JP | 05-177143 | 7/1993 |
| JP | 05-213919 | 8/1993 |
| JP | 05-237392 | 9/1993 |
| JP | 05-320150 | 12/1993 |
| JP | 08-027136 | 1/1996 |
| JP | 2001-523261 | 11/2001 |
| JP | 2002-020375 | 1/2002 |
| JP | 2002-080469 | 3/2002 |
| JP | 2003-192679 | 7/2003 |
| JP | 2003-192680 | 7/2003 |
| JP | 2003-231680 | * 8/2003 |
| JP | 2003-238544 | * 8/2003 |

* cited by examiner

*Primary Examiner*—Porfirio Nazario Gonzalez
(74) *Attorney, Agent, or Firm*—Peter F. Corless; Christine C. O'Day; Edwards Angell Palmer & Dodge LLP

(57) ABSTRACT

A novel multicomponent oxidation catalyst that can be effectively used in, for example, an epoxidation reaction of olefins, etc., being inexpensive and high in versatility and that exhibits high catalytic activity; and a process for producing an epoxy compound through hydrogen peroxide oxidation of an olefin with the use of the multicomponent oxidation catalyst. There is provided a multicomponent oxidation catalyst comprising a tungsten compound, a quaternary ammonium salt, any of phosphoric acids and/or boric acids and a hydrogen sulfate salt. Further, there is provided a process for producing an epoxy compound, characterized in that an olefin is oxidized with hydrogen peroxide in the presence of the above multicomponent oxidation catalyst. The epoxy compound obtained by this process is useful as an intermediate of agricultural chemicals, medicines or the like, a raw material of various polymers, etc.

7 Claims, No Drawings

MULTICOMPONENT OXIDATION CATALYST AND PROCESS FOR PRODUCING EPOXY COMPOUND THEREWITH

TECHNICAL FIELD

The present invention relates to an oxidation reaction using hydrogen peroxide as an oxidizing agent in the presence of a tungsten compound. More specifically, the present invention relates to an epoxidation reaction of olefins using said oxidizing agent. An epoxy compound obtained according to the present invention is useful as an intermediate for agricultural chemicals or medicines and a raw material for various polymers, and the like.

BACKGROUND ART

Conventionally, various reactions for epoxidizing olefins using a tungsten compound and hydrogen peroxide as oxidizing agents together with a co-catalyst have been known. For example, Patent document 1: JP-A-8-27136 describes a process for epoxidation using α-aminomethylphosphonic acid and a phase-transfer catalyst.

Further, Patent document 2: JP-A-2003-192679 and Patent document 3: JP-A-2003-192680 describe a process for epoxidizing olefins by adding hydrogen peroxide to a two-phase solution composed of an organic phase containing an olefin compound and a quaternary ammonium salt and an aqueous phase containing a tungsten compound and phosphoric acid or the like.

However, since none of these processes can provide a sufficient catalytic activity for some substrates to be oxidized, and in the former process, α-aminomethylphosphonic acid as an essential component is expensive, etc., development of a novel oxidation catalyst being inexpensive and high in versatility and that exhibits high catalytic activity has been desired.

As mentioned above, documents for prior art relating to the present invention include Patent document 1: JP-A-8-27136, Patent document 2: JP-A-2003-192679 and Patent document 3: JP-A-2003-192680, and these documents have been incorporated herein by reference.

DISCLOSURE OF INVENTION PROBLEM TO BE SOLVED BY THE INVENTION

The present invention has been made considering the above circumstance, and an object of the present invention is to provide a novel multicomponent oxidation catalyst that can be effectively used in, for example, an epoxidation reaction of olefins, etc. being inexpensive and high in versatility and that exhibits high catalytic activity.

MEANS FOR SOLVING THE PROBLEM

The inventors of the present invention have, after extensively studying a way to solve the above problem, found that a multicomponent oxidation catalyst comprising a tungsten compound, hydrogen peroxide, a quaternary ammonium salt, any of phosphoric acids and/or boric acids, and a hydrogen sulfate salt has high catalytic activity and high versatility, and further that epoxidation reaction can proceed smoothly by using said catalyst without using an agent etc. being expensive or cumbersome in preparation, and finally completed the present invention.

Thus, the present invention relates to a multicomponent oxidation catalyst comprising a tungsten compound, a quaternary ammonium salt, any of phosphoric acids and/or boric acids, and a hydrogen sulfate salt.

Further, the present invention relates to a process for producing an epoxy compound, characterized in that an olefin is oxidized with hydrogen peroxide in the presence of the above multicomponent oxidation catalyst.

EFFECTS OF THE INVENTION

By conducting oxidation reaction with hydrogen peroxide using the multicomponent oxidation catalyst of the present invention, various cyclic or non-cyclic olefins can be converted to corresponding epoxy compounds easily and in high yield.

BEST MODE FOR CARRYING-OUT THE INVENTION

The multicomponent oxidation catalyst according to the present invention means an oxidation catalyst system comprising, in addition to a so-called oxidation catalyst which exhibits a catalytic action alone, an auxiliary component having an enhancing action to the catalytic action exhibited by the main component alone, for example, a co-catalyst and the like.

The tungsten compound used in the multicomponent oxidation catalyst of the present invention include, for example, tungstate such as sodium tungstate, potassium tungstate and ammonium tungstate, and hydrates thereof; 12-tungstophosphoric acid, and salts such as sodium, potassium and ammonium, and hydrates thereof. Among them, sodium tungstate and hydrate thereof are preferable. The tungsten compound may be used alone or in combination of two or more members. Amount of the tungsten compound to be used is not particularly limited, and 0.001 to 1.0 mol, preferably 0.005 to 0.05 mol as a converted value to 1 gram atom of tungsten based on 1 mol of double bond in olefin.

The quaternary ammonium salt used in the present invention includes, for example, trioctylmethylammonium chloride, trioctylethylammonium chloride, dilauryldimethylammonium chloride, lauryltrimethylammonium chloride, stearyltrimethylammonium chloride, lauryldimethylbenzylammonium chloride, stearyldimethylammonium chloride, tricaprylmethylammonium chloride, tetrabutylammonium chloride, benzyltrimethylammonium chloride and benzyltriethylammonium chloride, and also bromides and iodides thereof instead of the chlorides. Among these quaternary ammonium salts, trioctylmethylammonium chloride is particularly preferable.

The quaternary ammonium salt may be used alone or in combination of two or more members. Amount of the quaternary ammonium salt to be used is preferably in a range of 0.1 to 10 times by mol, and more preferably in a range of 0.2 to 2 times by mol to one atom of tungsten.

The phosphoric acids used in the present invention include, for example, phosphoric acid, polyphosphoric acid, pyrophosphoric acid, sodium phosphate, potassium phosphate, ammonium phosphate, sodium hydrogen phosphate, potassium hydrogen phosphate and ammonium hydrogen phosphate, and phosphoric acid is more preferable. Amount of the phosphoric acids to be used is preferably in a range of not less than 0.1 to 1.0 time by mol, and more preferably in a range of not less than 0.2 to 2 times by mol as an equivalent of phosphor contained in said phosphoric acids based on one atom of tungsten.

The boric acids include, for example, boric acid, ammonium borate, alkaline metal salts of boric acid such as sodium borate and potassium borate, and alkaline metal salts of perboric acid such as sodium perborate. Among these boric acids, a hydrate thereof may be used where the hydrate is present. Further, for example, an alkaline metal salt of boric acid may be prepared by reacting boric acid with an alkaline metal hydroxide. Amount of boric acids to be used is usually 0.1 to 4 times by mol, and preferably 0.3 to 2 times by mol to one mol of a tungsten compound.

The hydrogen sulfate salt used in the present invention includes, for example, sodium hydrogen sulfate and hydrate thereof, potassium hydrogen sulfate and ammonium hydrogen sulfate, and sodium hydrogen sulfate and hydrate thereof are more preferable. Amount of the hydrogen sulfate salt to be used is usually 0.5 to 20 times by mol, preferably 1 to 10 times by mol, and more preferably 2 to 8 times by mol to one atom of tungsten.

Hydrogen peroxide as an oxidizing agent used in the process for producing an epoxy compound according to the present invention is easily available as a 10 to 60% by weight of hydrogen peroxide aqueous solution, and generally a commercially available aqueous solution can be used as it is or after appropriately diluted with water. Concentration of hydrogen peroxide is not particularly limited, but preferably in a range of 10 to 50% by weight, and more preferably in a range of 30 to 40% by weight in view of safety, reaction efficiency, etc. Amount of hydrogen peroxide to be used is preferably in a range of 1 to 3 mol, and more preferably in a range of 1.2 to 2 mol to one mol of double bond contained in olefin in view of conversion rate, selectivity, etc.

The olefin used in the process for producing an epoxy compound according to the present invention include, for example, olefins represented by the following general formula (I):

[Formula 1]

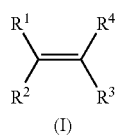

(I)

(wherein $R^1$, $R^2$, $R^3$ and $R^4$ each represent independently a hydrogen atom, alkyl group which may have substituent (s), aryl group which may have substituent(s), alkenyl group which has one or more non-conjugated carbon-carbon double bond and may have substituent(s), alkoxy group which may have substituent(s), acyl group which may have substituent (s), alkoxycarbonyl group which may have substituent (s), heterocyclic group, or carboxyl group or salt thereof); or the general formula (II):

[Formula 2]

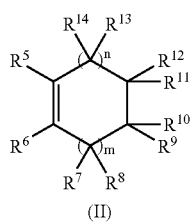

(II)

(wherein $R^5$, $R^6$, $R^7$, $R^8$, $R^9$, $R^{10}$, $R^{11}$, $R^{12}$, $R^{13}$ and $R^{14}$ each represent independently a hydrogen atom, alkyl group which may have substituent(s), aryl group which may have substituent(s), alkenyl group which has one or more non-conjugated carbon-carbon double bond and may have substituent(s), alkoxy group which may have substituent(s), acyl group which may have substituent(s), alkoxycarbonyl group which may have substituent(s), heterocyclic group, or carboxyl group or salt thereof; further, any two or more groups of these $R^5$ to $R^{14}$ may form a ring together with carbon atoms to which they link; m and n each represent independently an integer of 0 to 4 with a proviso that both of m and n are not 0 at the same time).

In the above general formula (I), the alkyl group represented by $R^1$, $R^2$, $R^3$ and $R^4$ includes, for example, a linear or a branched or cyclic alkyl group, specifically, for example, a linear or a branched alkyl group such as methyl group, ethyl group, n-propyl group, isopropyl group, n-butyl group, sec-butyl group, isobutyl group, tert-butyl group, n-pentyl group, neopentyl group, tert-pentyl group, hexyl group, heptyl group, octyl group, nonyl group, decyl group, cetyl group and stearyl group, and a cycloalkyl group such as cyclopentyl group, cyclohexyl group and cyclooctyl group. These alkyl groups may have substituent(s), and the substituent includes, for example, alkyl group described above; halogen atom such as fluorine atom, chlorine atom and bromine atom; alkoxy group such as methoxy group, ethoxy group, n-propoxy group, isopropoxy group and tert-butoxy group; hydroxy group; nitro group; carboxyl group; alkoxycarbonyl group such as methoxycarbonyl group and ethoxycarbonyl group; and acyloxy group such as acetoxy group and propionyloxy group.

The aryl group represented by $R^1$, $R^2$, $R^3$ and $R^4$ includes, for example, phenyl group and naphthyl group, and these aryl groups may have substituent(s). The substituent includes, for example, alkyl group described above; halogen atom such as fluorine atom, chlorine atom and bromine atom; alkoxy group such as methoxy group, ethoxy group, n-propoxy group, isopropoxy group and tert-butoxy group; hydroxy group; nitro group; carboxyl group; alkoxycarbonyl group such as methoxycarbonyl group and ethoxycarbonyl group; acyl group such as acetyl group, propionyl group and benzoyl group; and acyloxy group such as acetoxy group and propionyloxy group.

The alkenyl group which has one or more carbon-carbon double bond represented by $R^1$, $R^2$, $R^3$ and $R^4$ includes those where a plurality of carbon-carbon double bond in the group are in a non-conjugated state with one another and also said carbon-carbon double bond is in a non-conjugated state with the carbon-carbon double bond shown in the above general formula (I). Specific examples of these alkenyl groups include, for example, allyl group, methallyl group, prenyl group, 7-octenyl group, neryl group and geranyl group. These alkenyl group may have substituent(s), and the substituent includes, for example, alkyl group described above; halogen atom such as fluorine atom, chlorine atom and bromine atom; alkoxy group such as methoxy group, ethoxy group, n-propoxy group, isopropoxy group and tert-butoxy group; nitro group; carboxyl group; alkoxycarbonyl group such as methoxycarbonyl group and ethoxycarbonyl group; and acyloxy group such as acetoxy group and propionyloxy group.

The alkoxy group represented by $R^1$, $R^2$, $R^3$ and $R^4$ includes, for example, methoxy group, ethoxy group, n-propoxy group, isopropoxy group and tert-butoxy group, and the acyl group includes, for example, acyl group such as acetyl group, propionyl group and benzoyl group. The alkoxycarbonyl group includes, for example, methoxycarbonyl group and ethoxycarbonyl group.

The heterocyclic group represented by $R^1$, $R^2$, $R^3$ and $R^4$ preferably includes, for example, a 4 to 7-membered lactone ring or a 4 to 7-membered lactam ring.

In addition, each group represented by $R^5$, $R^6$, $R^7$, $R^8$, $R^9$, $R^{10}$, $R^{11}$, $R^{12}$, $R^{13}$ and $R^{14}$ in the general formula (II) includes the similar groups as described in the explanation for $R^1$, $R^2$, $R^3$ and $R^4$ of the above-described general formula (I).

Further, the ring formed by any two or more groups of these $R^5$, $R^6$, $R^7$, $R^8$, $R^9$, $R^{10}$, $R^{11}$, $R^{12}$, $R^{13}$ and $R^{14}$ together with carbon atoms to which they link, may be any of an aliphatic ring or an aromatic ring, and may be an aliphatic or an aromatic hetero ring which may contain a hetero atom such as oxygen atom, nitrogen atom and sulfur atom therein.

Specific examples of the olefins represented by the general formula (I) include, for example, linear olefin such as propylene, 1-butene, 2-butene, 1-pentene, 2-pentene, 3-pentene, 1-hexene, 2-hexene, 3-hexene, 1-heptene, 2-heptene, 3-heptene, 1-octene, 2-octene, 3-octene, 4-octene and 1-decene; branched olefin such as 3,3-dimethyl-1-butene, 4-methyl-2-pentene, 2-methyl-2-pentene, 3-methyl-2-pentene, 2,3-dimethyl-2-butene, 2,4,4-trimethyl-2-pentene, 2-methyl-2-heptene, and 2,3,4-trimethyl-2-pentene; halogenated olefin such as 5-chloro-2-methyl-2-pentene, citronellyl bromide, citronellyl chloride, geranyl chloride and geranyl bromide; olefin substituted with a hydroxy group such as isopulegol; aromatic olefin such as styrene and 1-phenyl-1-propene; ester type olefin such as methyl acrylate, methyl methacrylate, geranyl acetate, neryl acetate, citronellyl acetate, farnesyl acetate, isophityl acetate and methyl cinnamate; ketone type olefin such as methyl vinyl ketone and mesityl oxide; and linear non-conjugated diene such as 1,5-hexadiene, 1,7-octadiene and 1,9-decadiene.

Specific examples of the olefins represented by the general formula (II) include, for example, cycloolefin such as cyclohexene, cyclooctene, cyclododecene, 1-methylcyclohexene, 4-isopropyl-1-methylcyclohexene, 1,5-dimethylcyclooctene and 1,2,3,3-tetramethylcyclohexene; halogenated cycloolefin such as 1-chloro-3-cyclohexene; alkoxycycloolefin such as 1-methoxy-3-cyclohexene; ester type cycloolefin such as 1-acetoxy-2-cyclohexene; and ketone type cycloolefin such as 1-acetyl-2-cyclohexene.

Further, in the general formula (II), specific examples of the olefins having a ring, which is formed by any two or more groups of $R^5$, $R^6$, $R^7$, $R^8$, $R^9$, $R^{10}$, $R^{11}$, $R^{12}$, $R^{13}$ and $R^{14}$ together with carbon atoms to which they link and may also contain a hetero atom such as oxygen atom, nitrogen atom and sulfur atom therein, include, for example, bicyclic compound such as pinene, norbornene, bornene, 2,7,7-trimethyl-2-norbornene and octahydronaphthalene; and tricyclic compound such as 8-oxabicyclo[4.3.0]-3-nonene-7-one, 4-oxatricyclo[5.2.1.0$^{2,6}$]-8-decene-3-one, (7 or 1)-isopropyl-(1 or 7)-methyl-4-oxatricyclo[5.2.2.0$^{2,6}$]-8-dodecene-3-one.

The epoxy reaction according to the present invention can be illustrated by, for example, the following scheme.

[Formula 3]

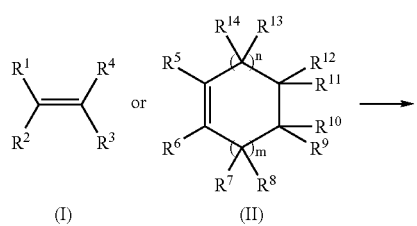

(I)    (II)

-continued

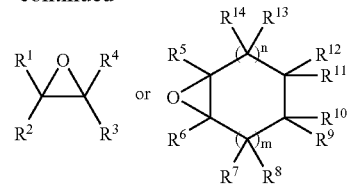

The process for producing an epoxy compound according to the present invention may be conducted in the presence or absence of a solvent. The solvent includes, for example, aliphatic hydrocarbon such as hexane, heptane, cyclohexane, methylcyclohexane, cyclooctane and 2,6-dimethylcyclooctane; aromatic hydrocarbon such as toluene, xylene, mesitylene, ethylbenzene and cumene. Among them, aromatic hydrocarbons such as toluene and xylene are preferable. Amount of solvent to be used is not particularly limited, but preferably a range of 0.1 to 50 times by weight, and more preferably a range of 0.2 to 20 times by weight to olefins in view of workability, etc.

The production process of the present invention may occasionally become two-phase system of an organic phase and an aqueous phase depending on the solvent to be used, and even in such case, the reaction proceeds smoothly.

Reaction temperature is not particularly limited so long as autolysis rate of hydrogen peroxide can be maintained at a low level and also selectivity for desired product can be maintained at a high level. The reaction temperature is usually selected within a range of 0 to 90° C., and preferably 20 to 60° C.

Reaction time naturally differs and fluctuates depending on reaction conditions such as reaction temperature, reaction solvent, molar ratios of raw materials to be used and the like, and is usually around several to several tens hours. When other reaction conditions are same, a longer reaction time generally gives a higher yield (conversion rate).

The production process of the present invention can be executed by either a process of consecutively adding a hydrogen peroxide aqueous solution to a reaction mixture containing any of olefins, a tungsten compound, a quaternary ammonium salt, any of phosphoric acids and a hydrogen sulfate salt, or a process of consecutively adding any of olefins to a reaction mixture containing a tungsten compound, a quaternary ammonium salt, any of phosphoric acids, a hydrogen sulfate salt and an hydrogen peroxide aqueous solution.

Further, the production process of the present invention sometimes gives an improved selectivity depending on acidity of the reaction mixture. A value of pH is preferably 1 to 6, and more preferably 1.5 to 3. Adjustment of pH can be performed with an inorganic acid such as sulfuric acid and hydrochloric acid; an inorganic base such as sodium hydroxide and sodium carbonate; or an organic base such as triethylamine, if necessary.

The thus obtained epoxy compound can be separated and obtained from the reaction mixture by means of a conventional procedure such as liquid separation, distillation, crystallization and various types of chromatography. Prior to carrying out such separation and purification procedures, the reaction mixture is desirably treated with a reducing agent such as sodium sulfite and sodium thiosulfate.

Here, contents described in the specification of JP Application No. 2003-417188 are incorporated herein in entirety thereof by reference.

Hereinbelow, the present invention will be explained more specifically using examples, however, the present invention should not be construed to be limited to these Examples.

Each abbreviation expresses the following meaning.
Oct=n-octyl group
Me=methyl group

EXAMPLE 1

Epoxidation of L-isopulegol

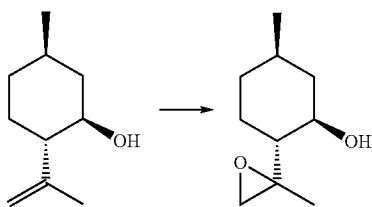

[Formula 4]

Into a 500 mL 4 necked flask equipped with a stirrer and a reflux condenser, $NaWO_4 \cdot 2H_2O$ (6.60 g, 0.02 mol), $NaHSO_4 \cdot H_2O$ (6.90 g, 0.05 mol), [(Oct)$_3$MeN]Cl (4.04 g, 0.01 mol), 85% $H_3PO_4$ (0.98 g, 0.0085 mol), toluene (77 g) and water (10 g) were charged. After adjusting pH of the solution to 4.0 with a 20% NaOH aqueous solution (5.8 g), L-isopulegol (77.1 g, 0.5 mol) was added thereto, and a 30% $H_2O_2$ aqueous solution (85 g, 0.75 mol) was added drop-wise at a temperature in a range of 35 to 40° C. for 1.5 hours with stirring. After the reaction mixture was stirred at 40° C. for further 10 hours, a 20% sodium sulfite aqueous solution (161 g, 0.26 mol) was added drop-wise to the reaction liquid at 40° C. or lower with stirring. After left for standing, an organic layer was separated, and the resulting organic layer was washed twice with water (100 g), and then the solvent was distilled off under reduced pressure to obtain a crude epoxide (83.8 g). The epoxide was distilled with a Claisen distiller to obtain 71.0 g of isopulegol epoxide (GC purity: 95.6%, boiling point: 93° C./533 Pa). Yield was 83% based on isopulegol.

EXAMPLE 2

Epoxidation of (7 or 1)-Isopropyl-(1 or 7)-methyl-4-oxatricyclo[5.2.2.0$^{2,6}$]-8-dodecene-3-one

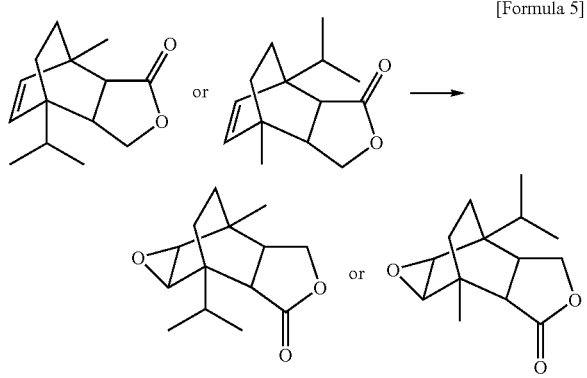

[Formula 5]

Into a 2 L reaction flask, toluene (251.6 g), 86% [(Oct)$_3$MeN]Cl (12.38 g., 0.0263 mol), $NaWO_4 \cdot 2H_2O$ (17.38 g, 0.0527 mol), $NaHSO_4 \cdot H_2O$ (18.2 g, 0.1317 mol), 85% $H_3PO_4$ (3.04 g, 0.0263 mol) and a 30% $H_2O_2$ aqueous solution (477.85 g, 4.2150 mol) were charged. After the mixture was stirred at room temperature for 30 minutes, a solution of an olefin compound (580.4 g, 2.6344 mol) in toluene (251.6 g) was added drop-wise thereto at a temperature in a range of 40 to 50° C. After the drop-wise addition was completed, the reaction mixture was stirred at 50° C. for 24 hours, then added drop-wise into a 20% $Na_2SO_3$ aqueous solution (2025.46 g, 3.2140 mol) at 20° C. or lower with stirring. After leaving for standing, an organic layer was separated, washed twice with water (1160.78 g), and then the toluene was distilled off to obtain 675 g of crude epoxide (GC purity: 83.40%) in 90.34% yield.

EXAMPLE 3

Epoxidation of (7 or 1)-Isopropyl-(1 or 7)-methyl-4-oxatricyclo[5.2.2.0$^{2,6}$]-8-dodecene-3-one

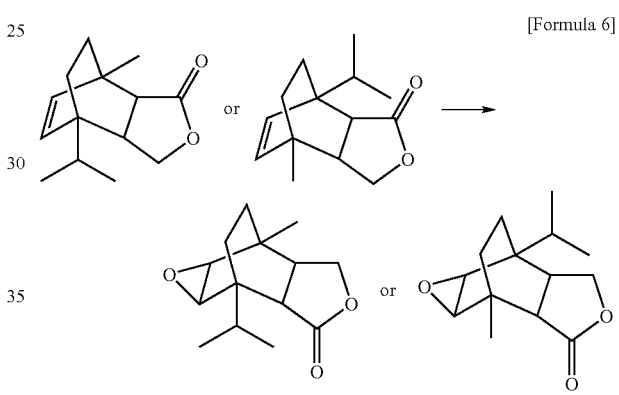

[Formula 6]

$NaWO_4 \cdot 2H_2O$ (0.54 g, 1.62 mmol), [(Oct)$_3$MeN]Cl (0.33 g, 0.812 mmol), $NaHSO_4 \cdot H_2O$ (0.56 g, 4.06 mmol) and 85% $H_3PO4$ (0.09 g, 0.812 mmol) were added into a solution prepared by dissolving an olefin compound (17.90 g, 81.2 mmol) in toluene (18 g). A 30% $H_2O_2$ aqueous solution (13.80 g, 121.8 mmol) was then added drop-wise thereto while temperature was maintained at 50° C. or lower in a water bath, and the reaction mixture was stirred at 50° C. for further 14 hours to proceed with the reaction. After completion of the reaction, a sodium sulfite aqueous solution was added drop-wise thereto while cooled in a ice bath with stirring. An organic layer was separated, washed with water, and concentrated to obtain 21.84 g of an epoxide (GC purity: 84.23%) in 95.83% yield as a white solid.

EXAMPLE 4

A reaction was carried out under the same conditions and in the same molar ratios of raw materials as in Example 3 except that the reaction time was shorten from 14 hours to 5 hours, and a conversion rate from the olefin compound to the epoxide was measured.

The results are shown in Table 1. In the table, % by mol is based on an olefin compound as a substrate. And conversion rate was measured using GC.

A reaction was carried out under the same conditions and in the same molar ratios of raw materials as in Example 3 except that the hydrogen sulfate salt was reduced from 5% by mol to 2% by mol and that the reaction time was shorten from 14 hours to 2 hours, and a conversion rate from the olefin compound to the epoxide was measured.

The results are shown in Table 1. In the table, % by mol is based on an olefin compound as a substrate. And conversion rate was measured using GC.

COMPARATIVE EXAMPLES 1 TO 5

In Example 3, each component of the multicomponent catalyst was variously changed and each result is shown in the tables 1-5 respectively. Further, experimental procedures were in accordance with those in Example 3, and reaction temperature was 50° C. in any case.

The results are shown in Table 1 together. In the table, % by mol is based on the olefin compound as a substrate. And conversion rate was measured using GC.

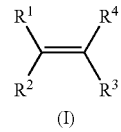

[Formula 7]

(I)

(wherein $R^1$, $R^2$, $R^3$ and $R^4$ each represent independently a hydrogen atom, alkyl group which may have substituent(s), aryl group which may have substituent(s), alkenyl group which has one or more non-conjugated carbon—carbon double bond and may have substituent(s), alkoxy group which may have substituent(s), acyl group which may have substituent(s), alkoxycarbonyl group which may have substituent(s), heterocyclic group, or carboxyl group or salt thereof).

TABLE 1

| | Tungstate | % by mol | Quaternary ammonium salt | % by mol | Acid | % by mol | Hydrogen sulfate salt | % by mol | Reaction time (hr) | Conversion rate (%) |
|---|---|---|---|---|---|---|---|---|---|---|
| Comparative Example | | | | | | | | | | |
| 1 | $Na_2WO_4 \cdot 2H_2O$ | 5 | | | | | | | 5 | 0 |
| 2 | $Na_2WO_4 \cdot 2H_2O$ | 5 | $\{(Oct)_3MeN\}Cl$ | 5 | | | | | 3 | 1.10% |
| 3 | $Na_2WO_4 \cdot 2H_2O$ | 2 | $\{(Oct)_3MeN\}Cl$ | 1 | $H_3PO_4$ | 1 | | | 6 | 27.10% |
| 4 | $Na_2WO_4 \cdot 2H_2O$ | 2 | $\{(Oct)_3MeN\}Cl$ | 1 | $H_2SO_4$ | 1 | | | 3 | 4.30% |
| 5 | $Na_2WO_4 \cdot 2H_2O$ | 2 | $\{(Oct)_3MeN\}Cl$ | 1 | | | $NaHSO_4$ | 2 | 3 | 5.40% |
| Example | | | | | | | | | | |
| 4 | $Na_2WO_4 \cdot 2H_2O$ | 2 | $\{(Oct)_3MeN\}Cl$ | 1 | $H_3PO_4$ | 1 | $NaHSO_4$ | 5 | 6 | 73.10% |
| 5 | $Na_2WO_4 \cdot 2H_2O$ | 2 | $\{(Oct)_3MeN\}Cl$ | 1 | $H_3PO_4$ | 1 | $NaHSO_4$ | 2 | 3 | 30.40% |

As clearly found from Table 1, a case when hydrogen sulfate salt is not used always shows a low conversion rate, and similarly a case when hydrogen sulfate salt is used but acid is not used also shows a low conversion rate.

INDUSTRIAL APPLICABILITY

The epoxy compound obtained by the process according to the present invention is useful as an intermediate for agricultural chemicals and medicines and a raw material for various polymers, etc.

What is claimed is:

1. A multicomponent oxidation catalyst comprising a tungsten compound, a quaternary ammonium salt, any of phosphoric acids and/or boric acids, and a hydrogen sulfate salt, with the proviso that the quarternary ammonium salt and the hydrogen sulfate salt are not the same salt.

2. The multicomponent oxidation catalyst according to claim 1, wherein said catalyst is used for producing an epoxy compound by oxidizing any of olefins with hydrogen peroxide.

3. The multicomponent oxidation catalyst according to claim 2, wherein said olefins are represented by the general formula (I)

4. A process for producing an epoxy compound, characterized in that any of olefins is oxidized with hydrogen peroxide in the presence of the multicomponent oxidation catalyst according to claim 1.

5. The process for producing an epoxy compound according to claim 4, wherein said olefins are represented by the general formula (I):

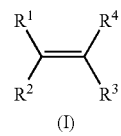

[Formula 9]

(I)

(wherein $R^1$, $R^2$, $R^3$ and $R^4$ each represent independently a hydrogen atom, alkyl group which may have substituent(s), aryl group which may have substituent(s), alkenyl group which has one or more non-conjugated carbon-carbon double bond and may have substituent(s), alkoxy group which may have substituent(s), acyl group which may have substitutent(s), alkoxycarbonyl group which may have substituent(s), heterocyclic group, or carboxyl group or salt thereof.

6. The process for producing an epoxy compound according to claim 4, wherein said olefins are represented by the general formula (II):

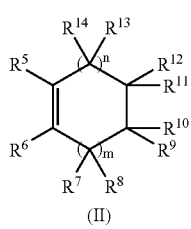

(II)

[Formula 10]

(wherein $R^5$, $R^6$, $R^7$, $R^8$, $R^9$, $R^{10}$, $R^{11}$, $R^{12}$, $R^{13}$ and $R^{14}$ each represent independently a hydrogen atom, alkyl group which may have substituent(s), aryl group which may have substituent(s), alkenyl group which has one or more non-conjugated carbon—carbon double bond and may have substituent(s), alkoxy group which may have substituent(s), acyl group which may have substituent(s), alkoxycarbonyl group which may have substituent(s), heterocyclic group, or carboxyl group or salt thereof, further, any two or more groups of these $R^5$ to $R^{14}$ may form a ring together with carbon atoms to which they link; m and n each represent independently an integer of 0 to 4 with a proviso that both of m and n are not 0 at the same time).

7. The multicomponent oxidation catalyst according to claim 2, wherein said olefins are represented by the general formula (II):

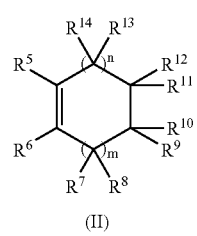

(II)

[Formula 8]

(wherein $R^5$, $R^6$, $R^7$, $R^8$, $R^9$, $R^{10}$, $R^{11}$, $R^{12}$, $R^{13}$ and $R^{14}$ each represent independently a hydrogen atom, alkyl group which may have substituent(s), aryl group which may have substituent(s), alkenyl group which has one or more non-conjugated carbon—carbon double bond and may have substituent(s), alkoxy group which may have substituent(s), acyl group which may have substituent(s), alkoxycarbonyl group which may have substituent(s), heterocyclic group, or carboxyl group or salt thereof. Further, any two or more groups of these $R^5$ to $R^{14}$ may form a ring together with carbon atoms to which they link; m and n each represent independently an integer of 0 to 4 with a proviso that both of m and n are not 0 at the same time).

\* \* \* \* \*